United States Patent [19]
Kaufman et al.

[11] Patent Number: 5,770,585
[45] Date of Patent: Jun. 23, 1998

[54] HOMOGENEOUS WATER-IN-PERFLUOROCHEMICAL STABLE LIQUID DISPERSION FOR ADMINISTRATION OF A DRUG TO THE LUNG OF AN ANIMAL

[76] Inventors: Robert J. Kaufman, 8129 Stanford Ave., University City, Mo. 63130; Thomas J. Richard, 8607 Rowland Ave., University City, Mo. 63132; Richard A. Stephens, 11951 Stonywood Dr., St. Louis, Mo. 63122; Thomas H. Goodin, 311 Stephanie La., Manchester, Mo. 63011; John S. Allen, 1295 Chambers Rd., St. Louis, Mo. 63137; Tony E. Layton, 1112 Merlin La., Godfrey, Ill. 62035

[21] Appl. No.: 438,098

[22] Filed: May 8, 1995

[51] Int. Cl.$^6$ ................................................. A61K 31/685
[52] U.S. Cl. ........................... 514/78; 514/778; 514/772; 514/320; 514/199; 514/200; 514/601; 514/34; 514/35; 514/357
[58] Field of Search .................................... 514/320, 199, 514/200, 601, 34, 35, 357, 772, 778, 78

[56] References Cited

U.S. PATENT DOCUMENTS

| | | | |
|---|---|---|---|
| 3,911,138 | 10/1975 | Clark, Jr. | 424/3.52 |
| 4,569,784 | 2/1986 | Moore | 252/315.1 |
| 4,815,446 | 3/1989 | McIntosh | 600/3 |
| 4,975,468 | 12/1990 | Yiv | 514/759 |
| 4,990,283 | 2/1991 | Visca et al. | 252/309 |
| 5,158,536 | 10/1992 | Sekins et al. | 604/20 |
| 5,183,589 | 2/1993 | Brunetta et al. | 252/308 |

*Primary Examiner*—James J. Seidleck
*Assistant Examiner*—Michael A. Williamson
*Attorney, Agent, or Firm*—Wood,Herron & Evans, L.L.P.

[57] ABSTRACT

This invention is directed to a homogenous water-in-perfluorochemical stable liquid dispersion for acceptable therapeutic administration of a drug to the lung of an animal. The dispersion includes a perfluorochemical liquid, water, surfactant and drug, wherein the water is homogeneously dispersed in the perfluorochemical to form a stable water-in-perfluorochemical liquid dispersion. The perfluorochemical constitutes greater than 50% by volume of the dispersion, and the drug is contained in the dispersion in an effective therapeutic amount.

The invention further includes a method of delivering a drug to the lung of an animal. This aspect of the invention includes administering a stable homogenous water-in-perfluorochemical liquid dispersion to the animal lung or a section thereof. If desired, the method may further include delivering a breathable gas to the lung with a mechanical ventilator during the administration.

21 Claims, 1 Drawing Sheet

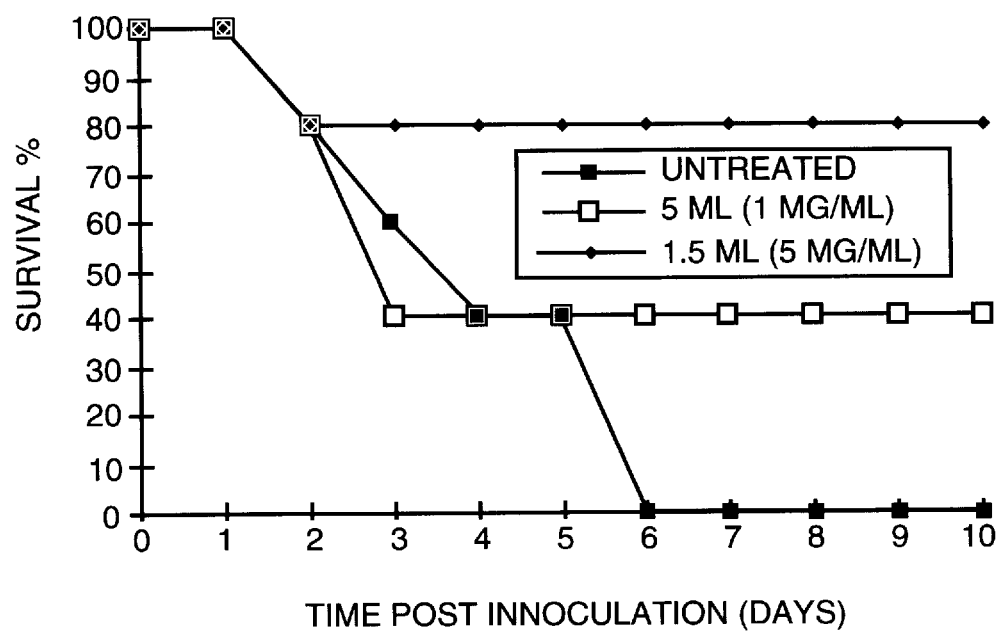

HOMOGENEOUS WATER-IN-PERFLUOROCHEMICAL STABLE LIQUID DISPERSION FOR ADMINISTRATION OF A DRUG TO THE LUNG OF AN ANIMAL

FIELD OF THE INVENTION

This invention relates to the use of perfluorochemicals in the lung and, more particularly, to inverted or water-in-perfluorochemical dispersions for therapeutic administration of a drug to the lung of an animal.

BACKGROUND OF THE INVENTION

Because of their characteristics, perfluorochemicals have been proposed for use as perfusates for organs, as blood substitutes and as liquids for liquid lavaging or liquid ventilation of the lungs. Perfluorocarbons are chemically inert materials that have long been known to enable oxygen transport in mammalian systems. For example, rats have been shown to survive total immersion in a liquid perfluorochemical saturated with oxygen. This experiment succeeds because the high solubility of oxygen in most perfluorochemicals enables the rat to "breathe" the perfluorochemical. This process, and its variants, are commonly referred to as liquid ventilation. In one form of liquid ventilation known as perfluorochemical assisted gas exchange (PAGE), a pure fluorochemical liquid is instilled to the lungs of an animal in an amount equal to the functional residual capacity of the lungs. The animal then is connected to a mechanical ventilator which delivers tidal volumes of a breathable gas to the lungs. However, the PAGE technique is extremely limited with respect to the ability to deliver drugs to the lungs. Because perfluorochemicals are both hydrophobic and lipophobic, very few medicaments other than halocarbon anesthetics may be delivered to the lungs using such liquid breathing techniques.

The use of perfluorochemical-in-water microemulsions has been proposed as a way of incorporating a water soluble drug in a formulation for intravenous administration. Yiv, U.S. Pat. No. 4,975,468. In addition, U.S. Pat. No. 5,158,536 to Sekins et al., suggests the use of an aqueous perfluorocarbon liquid emulsion as a way of delivering water soluble therapeutic agents to the pulmonary air passages in contact with or near a patient's lung cancer tumor sights. However, the low concentration of fluorochemical in such formulations is insufficient to allow oxygen exchange during liquid ventilation. Therefore, it would be extremely beneficial to have a formulation capable of administering a therapeutic agent to the lung of an animal and of providing sufficient oxygen exchange during liquid ventilation.

SUMMARY OF THE INVENTION

This invention is directed to a homogenous water-in-perfluorochemical stable liquid dispersion for acceptable therapeutic administration of a drug to the lung of an animal. The dispersion includes a perfluorochemical liquid, water, surfactant and drug, wherein the water is homogeneously dispersed in the perfluorochemical to form a stable water-in-perfluorochemical liquid dispersion. The perfluorochemical constitutes greater than 50% by volume of the dispersion, and the drug is contained in the dispersion in an effective therapeutic amount.

By way of example, the perfluorochemical may be perfluoro-n-butyltetrahydrofuran, perfluorodichlorooctane, perfluorobischlorobutylether, perfluorodecalin, perfluoromethyldecalin, perfluorodimethyldecalin, perfluorodimethyladamantane, perfluorooctylbromide, perfluoro-4-methyl-octahydroquinolidizine, perfluoro-N-methyl-decahydroquinoline, F-methyl-1-oxa-decalin, perfluoro-bicyclo(5.3.0)-decane, perfluorooctahydroquinolidizine, perfluoro-5,6-dihydro-5-decene, and perfluoro-4,5-dihydro-4-octene, chlorinated perfluorocarbons, or mixtures thereof.

The surfactant may be any synthetic or natural dialkyl or diacyl glyceryl phosphoryl choline, such as egg lecithin, a polyalkylene oxide, a fluorinated polyoxyethylene, or a mixture thereof.

The drug may be any drug which maintains homogeneity in the dispersed or continuous phase of the dispersion. For example, water soluble components are expected to disperse uniformly within the aqueous phase, where as lipophilic drugs are expected to be incorporated into the perfluorochemical phase, or at the interface of the perfluorochemical and inverse micelle. It is additionally contemplated that drugs capable of incorporation into lipid emulsion and/or liposomes could be utilized, even if they are not soluble in either perfluorochemicals or water, since the examples of this invention clearly show that egg phospholipid is uniformly dispersed in the aqueous phase. Examples of a few of the drugs which may be incorporated in the dispersion include doxorubicin, deoxyribonuclease enzyme, a vector containing a normal cystic fibrosis transmembrane conductance regulator gene, pentamidine isethionate, amphotericin, a $\beta_2$ agonist, methotrexate, etoposide, a phospholipid surfactant, a penicillin, a cephalosporin, a sulphadrug, and a prodrug of any of the foregoing drugs, or mixtures thereof. A prodrug is a synthetic derivative of any of the above drugs designed to increase or decrease the rate of administration, enhance the activity, or increase the solubility in either the aqueous or dispersed or continuous phase of an emulsion of this invention.

In general, the perfluorochemical is present in the dispersion in an amount greater than about 50% to about 99% by volume, and the water is present in an amount of from about 50% to about 1% by volume. However, preferably, the perfluorochemical is present in an amount of from about 85% to about 99% by volume, and the water is present in an amount of from about 15% to about 1% by volume to ensure physiological acceptability of the dispersion. Preferably, the surfactant is present in an amount of from about 0.5% to about 10% by weight and, more preferably, from about 1% to about 4% by weight. Furthermore, the drug typically is present in the dispersion in an amount from about 0.001% to about 3% by weight. However, this depends upon the particular drug incorporated into the dispersion and the condition to be treated. For example, the drug may be present in an amount sufficient to treat a lung condition such as cystic fibrosis, infant respiratory distress syndrome, a bacterial or fungal infection, asthma or lung cancer.

The invention further includes a method of delivering a drug to the lung of an animal. This aspect of the invention includes administering a stable homogenous water-in-perfluorochemical liquid dispersion to the animal lung or a section thereof. If desired, the method may further include delivering a breathable gas to the lung with a mechanical ventilator during the administration.

The inventive water-in-perfluorochemical liquid dispersion and method of delivering a drug to the lung of an animal offer several benefits and advantages. One of the primary advantages is the ability to incorporate and deliver a drug or drugs to the lung of an animal in a formulation which provides sufficient gas exchange during liquid ventilation.

Furthermore, delivery of such therapeutic agents by this method is an enormous improvement over current techniques, since the active agent is uniformly distributed across the entirety of the alveolar space, making it available to the distant small alveolar beds which are not accessible by nebulization or aerosol technologies. Furthermore, in the case of chemotherapeutics, systemic toxicity and consequent dosage limitations imposed by the requirement of intravenous infusion should be greatly reduced or even eliminated.

BRIEF DESCRIPTION OF THE DRAWING

The FIGURE shows survival of rats treated with water-in-perfluorochemical (WIP) penicillin dispersions four hours after bacterial inoculation.

DETAILED DESCRIPTION OF THE INVENTION

The stable liquid dispersions of the invention are "reverse micellar" water-in-perfluorochemical (WIP) dispersions, with the perfluorochemical liquid being the continuous phase. As used herein, the term "dispersion" refers to any dispersion, emulsion or microemulsion. As mentioned briefly above, the WIP dispersion includes a perfluorochemical liquid, water, surfactant and drug. The perfluorochemical constitutes greater than 50% by volume of the dispersion, and the water is homogeneously dispersed in the perfluorochemical along with a surfactant to form the stable WIP dispersion. Furthermore, the drug is contained in the dispersion in an effective therapeutic amount.

The perfluorochemical liquid may be any of a number of different perfluorochemicals. Suitable examples include perfluoro-n-butyltetrahydrofuran, perfluorodichlorooctane, perfluorobischlorobutylether, perfluorodecalin, perfluoromethyldecalin, perfluorodimethyldecalin, perfluorodimethyladamantane, perfluorooctylbromide, perfluoro-4-methyl-octahydroquinolidizine, perfluoro-N-methyl-decahydroquinoline, F-methyl-1-oxa-decalin, perfluoro-bicyclo(5.3.0)-decane, perfluorooctahydroquinolidizine, perfluoro-5,6-dihydro-5-decene, and perfluoro-4,5-dihydro-4-octene, chlorinated perfluorocarbons, and mixtures thereof.

The surfactant used in the WIP dispersion may be any of a number of different surfactants. However, because the liquid dispersion is used as a vehicle for delivering a drug to the lungs, it is preferred to use nonionic surfactants because these surfactants do not cause excessive irritation to pulmonary tissue. Suitable examples of surfactants which may be used in the WIP dispersion include egg yolk phospholipid, a perfluorochemical alcohol, a polyalkyleneoxide, a 1,2-dialkylglycero-3-phosphoryl choline, a 1,3-dialkylglycero-2-phosphoryl choline, a perfluorinated polyoxyethylene, and mixtures thereof. In a preferred form of the dispersion, the surfactant includes a fluorinated polyoxyethylene as taught by Yiv in U.S. Pat. No. 4,975,468 which is incorporated herein in its entirety by reference having the formula:

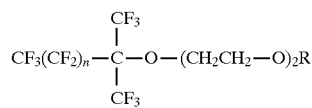

wherein n=5–11, z=3–12 and R=H or $CH_3$

One of the major benefits of the inventive WIP dispersion is the ability to incorporate either water soluble (hydrophilic) or water insoluble (lipophilic) drugs. Since perfluorochemicals are both hydrophobic and lipophobic, few medicaments (other than halocarbon based anesthetics) are soluble in neat perfluorochemicals. However, the WIP dispersion provides a delivery vehicle not only for drugs soluble in a perfluorochemical, but also for water soluble (hydrophilic) and lipid soluble (lipophilic) drugs. The WIP dispersion incorporates homogeneous solutions or dispersions of water soluble drugs in the aqueous micellar pools of the dispersion. Alternatively, drugs that are soluble in perfluorochemicals may be incorporated into the continuous phase. Lipophilic drugs that are not soluble in either water or perfluorochemicals may be dispersed at the interface between the surfactant and continuous phases, especially when phospholipids are employed as surfactants. Furthermore, oil in water emulsions or liposomes containing lipophilic drugs may serve as the dispersed phase of the formulation. Thus, any of a variety of drugs suitable for therapeutic administration to the lung may be incorporated in the WIP dispersion.

Depending on the particular drug or drugs incorporated in the WIP dispersion, the dispersion has specific utility in the treatment of lung conditions such as cystic fibrosis, infant respiratory distress syndrome (IRDS), meconium removal in neonates, bacterial infections, fungal infections, asthma and lung cancer, for example, and these particular uses are discussed in more detail below.

Cystic Fibrosis

Liquid ventilation using the WIP dispersion is believed to provide an avenue for two improvements in the treatment of cystic fibrosis. One is the delivery of DNAse, the enzyme that cleaves DNA into smaller, less viscous fragments, and the second is the delivery of a vector for the cystic fibrosis transmittance regulator gene.

The primary cause of pulmonary dysfunction in cystic fibrosis patients is thick airway secretions containing relatively high concentrations of cellular DNA liberated from disintegrated inflammatory cells. R. C. Hubbard, N. G. McElvaney, P. Birrer, S. Shak, W. Robinson, C. Jolley, M. Wu, M. Chernick, R. G. Crystal, "A preliminary study of Aerosolized Recombinant Human Deoxyribonuclease I in the Treatment of Cystic Fibrosis", *The New England Journal of Medicine*, 326 (12), 812 (1992). Because of the relatively high concentration of DNA in the secretions, they are viscous and difficult to expectorate. Recent research has resulted in the development of a recombinant human deoxyribonuclease enzyme (rhDNAse), which cleaves this cellular DNA into smaller fragments, thereby reducing the viscosity of the airway secretions. This product, made by Genentech, has been approved for use in the treatment of cystic fibrosis. The product is administered chronically, twice per day, via metered dose inhalers. It is expected that the number of treatments could be reduced by an order of magnitude if the lungs could be completely lavaged with the DNAse ingredient.

Another important application intended for WIP dispersions is as vehicles for the delivery of a modified adenovirus serving as a vector to deliver the normal cystic fibrosis transmembrane conductance regulator (CFTR) gene to the epithelial cells of the lung. Ever since the landmark articles on identification of the cystic fibrosis gene—(a) J. M. Robbens et al., "Identification of the Cystic Fibrosis Gene: Chromosome Walking and Jumping", *Science*, 245, 1059 (1989); (b) J. R. Riordan et al., "Identification of the Cystic Fibrosis Gene: Cloning and Characterization of Complementary DNA", *Science*, 245, 1066 (1989); and B. Kerem et al., "Identification of the Cystic Fibrosis Gene: Genetic Analysis," *Science*, 245, 1073 (1989)—intensive research has focused on transfection procedures for providing a normal copy of the gene, which would then express the protein responsible for modulation of chloride ion permeability through the cAMP pathway. The problem with most such transfection procedures is that they cannot supply the gene selectively to lung epithelium. Recently, the NIH, in conjunction with the Johns Hopkins School of Medicine, constructed a replication-deficient recombinant adenovirus containing a normal CFTR cDNA, and proved that it expressed human CFTR mRNA in lung epithelium and subepithelium after intratracheal administration to cotton rats. Rosenfeld, et al., "In Vivo Transfer of the Human Cystic Fibrosis Transmembrane Conductance Regulator Gene to the Airway Epithelium", Cell, 68, 143 (1992). Inclusion of this vector in the WIP dispersion should provide for uniform, selective delivery to airway epithelium.

Infant Respiratory Distress Syndrome

Pre-term neonates often present with infant respiratory distress syndrome (IRDS). Liquid ventilation employing pure (neat) perfluorochemical has been proposed to relieve the stress on the neonate lung that typically accompanies forced ventilation with high inspired oxygen content. T. H. Shaffer, M. R. Wolfson, and L. C. Clark, "Liquid Ventilation", Pediatric Pulmonology, 14, 102 (1992).

Unfortunately, the use of pure perfluorochemical in liquid ventilation does nothing to alleviate the cause of the problem, which is pulmonary surfactant deficiency. To address this need, two commercial surfactant formulations have been approved for intratracheal administration. Both Exosurf and Survanta are variants of the same theme—the delivery of phospholipid based surfactant to the lung. Exosurf is synthetic dipalmitoyl phosphatidyl choline, which is one of the components of natural surfactant. Although this compound reduces surface tension, it is ineffective in IRDS because it spreads and distributes poorly. To overcome this inadequacy, the commercial formulation includes cetyl alcohol (a solubilizer) and Tyloxapol (a co-surfactant). Survanta is a formulation of bovine lung extract designed to accomplish the same goal. Both have been linked with deficiencies in oxygenation and lung compliance due to pulmonary obstruction associated with the rather difficult dosing procedure.

However, with the inventive WIP dispersion, egg yolk phospholipid may be used as the therapeutic "drug". Egg yolk phospholipid consists primarily of palmitoyl, linoleyl, and linolenoyl phosphatidyl cholines and the corresponding phosphatidyl ethanolamines with the remaining components being minor agents such as sphingomyelin and phosphatidyl inositol. Such surfactants may be dispersed into the aqueous phase of the WIP dispersion. This formulation is expected to provide a simple, reliable and reproducible method for the distribution of surfactant across the neonate alveoli. Liquid ventilation with such a formulation should prevent the adverse effects associated with pulmonary obstruction, since both oxygen and surfactant are uniformly distributed at the alveolar interface.

Removal of Meconium

In an interesting study, Shaffer treated meconium stained lambs with perfluorocarbon ventilation, and showed an increase in lung compliance and a decrease in inspiratory elastic work of breathing during the ventilation process. T. H. Shaffer, C. A. Lowe, et al., "Liquid Ventilation: Effects on Pulmonary Function in Distressed Meconium-Stained Lambs", Pediatric Research, 18 (1), 47 (1984). The problem with this approach is that both lipophilic and hydrophilic substances repel fluorocarbons, so it is difficult to actually remove meconium by this procedure. However, administration of the WIP dispersion should allow the meconium to slurry in the non-fluorocarbon phase of the dispersion increasing the efficacy of meconium removal upon expiration of the dispersion.

Pneumonia

Pentamidine isethionate is known to have activity against Pneumocystis Carinii and is approved for use in HIV-infected patients. It is insoluble in organic solvents, but is administered as an aqueous aerosol. It is estimated to reduce the risk of Pneumocystis Carinii Pneumonia (PCP) in high risk patients by 50–70%. Incorporation into the aqueous phase of the WIP dispersion should improve the efficacy of treatment by allowing the drug to access a significantly greater fraction of lung tissue than possible by aerosolization.

Fungal Infections of the Lung

HIV compromised patients often suffer from fungal infections of the lung, examples of which are bronchopulmonary aspergillosis, blastomycosis, coccidioidomycosis and cryptococcsis. Currently, treatment of these life threatening conditions involves intravenous infusion of amphotericin-B (Fungizone®). Unfortunately, this drug suffers from a severe dosage limitation due to its high renal toxicity. Liquid ventilation using the WIP dispersion provides an opportunity to administer the water soluble drug amphotericin topically to treat an invasive fungal infection of the lung, thereby reducing or eliminating the amount of amphotericin in the systemic circulation. Targeting amphotericin directly to the infected lung tissue should effectively eliminate the observed nephrotoxicity.

Asthma

Liquid ventilation techniques using the WIP dispersion may improve the efficacy of asthma treatments using the $\beta_2$ agonists.

Lung Cancer

A variety of chemotherapeutics have been developed for treatment of lung cancer, and many of them have been studied in conjunction with intravenously administered perfluorocarbon emulsion under carbogen breathing. B. A. Teicher, T. S. Herman and E. Frei, "Perfluorochemical Emulsions: Oxygen Breathing in Radiation Sensitization and Chemotherapy Modulation", Important Advances in Oncology, 39 (1992). In most cases, significant improvement is noted. Unfortunately, intravenous infusion is limited with respect to dosage and frequency of administration, because perfluorochemical emulsion particles are rapidly phagocytized by the cells of the reticuloendothelial system (RES), and accumulate primarily in the liver, spleen, and lung, causing significant enlargement of these organs. As currently formulated, the total dosage of most such emulsions is limited to under 4 cc/kg of perfluorochemical. This precludes multiple dosing regimens, which would be required for the chemotherapeutics available for cancer therapy. In addition, intravenous administration does not selectively target the lung. The WIP dispersion, however, provides a unique mechanism for selective, multiple dosage delivery of lung chemotherapeutics. RES deposition would not apply since the drugs would be administered intratracheally, and the perfluorochemical is expired after use.

Specific examples of drugs which have been approved for lung cancer therapy, and which could be delivered in the WIP dispersion include adriamycin (doxorubicin), methotrexate and etoposide. Teicher has already demonstrated that intravenous fluorocarbon infusion and carbogen breathing augment adriamycin and etoposide therapy. B. A. Teicher, S. A. Holden, et al., "Effects of Fluosol-DA and Oxygen Breathing on Adriamycin Antitumor Activity and Cardiac Toxicity in Mice", Cancer, 61, 2196 (1988); B. A. Teicher, S. A. Holden and C. M. Rose, "Effect of Oxygen on the Cytotoxicity and Antitumor Activity of Etopside", *Journal of the National Cancer Institute*, 75 (6), 1129 (1985). Removal of the dosage limit by the use of the WIP dispersion should greatly enhance the efficacy of this treatment modality.

Finally, the chemotherapeutics used in lung cancer therapy are themselves extremely toxic. Delivery of such agents by liquid ventilation should greatly ameliorate toxicity, since delivery is provided directly to lung epithelial cells, obviating the need for intravenous infusion of these noxious materials.

EXAMPLES OF WATER-IN-PERFLUOROCHEMICAL (WIP) DISPERSIONS

Example 1

A solution of the preferred fluorinated polyoxyethylene (0.03 g) in 1,8-perfluorodichlorooctane (8.80 g) was prepared. To this solution was added $H_2O$ (0.06 g). The mixture was sonicated (Fisher Sonic Dismembrator Model 300). At 37° C., a transparent liquid was obtained. Upon cooling to room temperature, the mixture became cloudy. However, reheating to 37° C. once again resulted in a clear liquid. Thus, at body temperature, this formulation produced a stable, clear liquid.

Example 2

A solution of the preferred fluorinated polyoxyethylene (0.18 g) in 1,8-perfluorodichlorooctane (8.28 g) was prepared. This resulted, after sonication, in a transparent, stable liquid at 37° C.

Example 3

A solution of the preferred fluorinated polyoxyethylene (0.09 g) in perfluorooctyl bromide (2.3 ml, 4.14 g) was prepared. To this solution was added a homogeneous 2% egg yolk lecithin dispersion (0.1 g of dispersion, prepared by homogenization of lecithin in $H_2O$). After sonication, a translucent liquid resulted, stable to storage at both 25° C. and 37° C. overnight. This is a tremendous improvement over current therapy, since it enables delivery to all areas of the lung, whereas conventional aerosolation or nebulization therapies access only 5–15% of the alveoli.

Example 4

To a 10×130 mm test tube was added the preferred fluorinated polyoxyethylene (0.091 g) and perfluorodichlorooctane (2.3 ml, 4.11 g), followed by a 5 mg/ml solution of doxorubicin (0.11 g). Brief sonication produced a stable, transparent emulsion, exhibiting a uniform deep red hue, characteristic of the dissolved doxorubicin. As a control, the same mixture was prepared omitting the preferred fluorinated polyoxyethylene. In this control, the doxorubicin aqueous phase simply floated to the top.

Example 5

Pluronic F-68 (1.6143 g) was placed in a glass vial. To the vial was also added $C_6F_{13}CH_2CH_2OH$ (9.11 g). After application of mild heat with agitation, a clear solution was obtained. To a portion of this still warm solution (2.2 g) was added FC-77 (perfluoro-n-butyltetrahydrofuran, 17.75 g) and $H_2O$ (0.0672 g). This resulted in a transparent liquid, which was stable to storage at 37° C. If kept at room temperature for more than a day, white crystals (presumably Pluronic-F68) formed, but the transparent liquid was restored by brief warming to 37° C. The composition of this solution on a weight to weight basis was:

| | |
|---|---|
| Pluronic-F-68 | 1.65% |
| $C_6F_{13}CH_2CH_2OH$ | 9.34% |
| FC-77 | 88.67% |
| $H_2O$ | 0.34% |

This example demonstrates that commonly used nonionic, nonperfluorinated surfactants can be used to homogeneously disperse water in a perfluorochemical if a perfluorochemical alcohol is used as the co-surfactant.

Rodent Model

The following protocol was used to test various perfluorochemical formulations in "liquid breathing" as presented in Examples 6–8 below. Male Sprague-Dawley rats ($\geq 250$ gms) were anesthetized with a mixture of ketamine (100 mg/kg) and xylazine (13 mg/kg) for catheterization of the right carotid artery. After the artery was dilated, the tip of a 15 cm PE-50 was advanced 1–2 cm into the lumen and secured into place with 4-0 silk ligatures. The catheter was then flushed with 5 U/ml heparin-saline and plugged with a pin. Samples (60–100µ)l from the carotid artery were obtained for the determination of blood gases ($PaO_2$, $PaCO_2$, pH, $HCO_3$, $\%O_2$ saturation, base excess) using a Corning Model 170 analyzer.

An endotracheal tube (ET) was inserted into the animal's trachea. The ET was fashioned from a 58 mm length of PE-260 tubing pulled to a 5 mm taper at the tip. A sterile, 16 gauge, luer-lock hypodermic needle was cut to a length of 10 mm and inserted into the non-tapered end of the PE tubing. The vocal folds and trachea were visualized by transillumination of the ventral neck and retracting of the tongue superiorly with a narrow bladed metal spatula. A few drops of 2% lidocaine were instilled into the pharynx to prevent spasm and facilitate insertion of the ET. The ET was advanced into the trachea until it met with resistance and the lung sounds were checked bilaterally to confirm the correct placement of the tube. The animal was then placed on a warming blanket heated to 37° C.

The 16 gauge needle hub of the ET was connected to a volume controlled rodent ventilator (Harvard, Model 683) and the tidal volume and respiration rate were set so that the $PaCO_2$ was between 35 and 45 mmHg at an $FiO_2$=0.21. The connection to the ventilator was via a three-way stopcock fitted with a strain gauge pressure transducer for measuring airway pressures (cm H2O; peak and plateau) and compliance. The pre- and post-treatment airway pressures were recorded continuously on a Narco MKS-III physiograph. A second baseline set of arterial blood gases were obtained at an $FiO_2$=1.0. The animal was disconnected from the ventilator and the WIP dispersion was instilled into the lungs equal to the functional residual capacity (FRC) volume (30 ml/kg). Prior to administration, the WIP dispersion was warmed to 37° C. and saturated with 100% oxygen. The animal was then reconnected to the ventilator with the $FiO_2$ remaining at 1.0. Arterial blood gas samples were collected at 5, 15 and 30 minutes during liquid ventilation. After the 30 minute blood sample was taken, the animal was disconnected from the ventilator and the WIP dispersion drained from the lungs by gravity into a graduated cylinder. The animal was reconnected to the ventilator and a blood gas sample was drawn 5 minutes after the WIP dispersion had been removed from the lungs. The carotid catheter was then removed and the surgical wound sutured. When the animal showed signs of spontaneous respiration, the ET was removed and the rat placed in an oxygen chamber with an $FiO_2=0.80–0.93$ overnight. On the following day, the rat was transferred into a standard cage and returned to the rodent colony.

Example 6

The invention is demonstrated in this Example wherein the perfluorochemical formulations listed in Table 1 were tested using the rodent model discussed above. Referring to Table 1, the formulations labelled WIP 1, WIP 2 and WIP 3 are water-in-perfluorochemical (WIP) dispersions made according to the principles of the present invention. In WIP1 and 2, the drug is lecithin, while in WIP 3, the drugs incorporated include lecithin and doxorubicin. The term "surfactant" in Table 1 refers to the preferred fluorinated polyoxyethylene presented in the detailed description above. "PFBTHF" is perfluoro-n-butyltetrahydrofuran and "$H_2O$ q.s." refers to make up water. PIW 40, PIW 10 and PIW 50 are perfluorochemical-in-water (PIW) formulations having the composition presented in Table 1; and PIW 10 and 50 are made according to the teachings of U.S. Pat. No. 4,975,468 to Yiv. PIW 40 contains 40% perfluorochemical by volume, while PIW 10 and PIW 50 contain 10% and 50% perfluorochemical by volume, respectively.

Tables 2 and 3 provide $pO_2$, pH and survival statistics for animals receiving each of the six formulations presented in Table 1. Note that the animals receiving the WIP dispersions of the present invention survived, while animals receiving the PIW formulations did not. Referring more particularly to Tables 2 and 3, arterial blood gas ($pO_2$) and pH measurements are shown for liquid breathing using the specific formulations. In both Table 2 and 3, baseline blood gas and pH measurements were taken while the animals were connected to the ventilator but before the particular formulation was instilled into the lungs. Baseline measurements were taken while the animals were breathing 21% $O_2$ and 100% $O_2$, and in all cases there was the expected increase in arterial $pO_2$, as shown in Table 2.

Tables 2 and 3 further include blood gas and pH measurements taken 30 minutes into the liquid breathing. As shown in Table 2, the $pO_2$ remains high only in the animals receiving the inventive WIP formulations 1, 2 and 3 of the inventive WIP dispersion. In stark contrast, however, the animals receiving the various perfluorochemical-in-water formulations showed extremely low $PO_2$ values 30 minutes into the liquid breathing. Furthermore, the animals receiving the perfluorochemical-in-water formulations became acidotic, having a pH less than 7.3 as shown in Table 3. In addition, the animals receiving the various formulations of the WIP dispersions all survived while the animals receiving the perfluorochemical in water formulations did not. Survival is defined as the ability to return the animal from the 100% $O_2$ used during liquid breathing to room air, recovery from anesthesia, and mostly normal behavior for two days after the procedure.

Example 7

$C_6F_{13}CH_2CH_2OH$ (0.30 g), the preferred fluorinated polyoxyethylene (0.53 g) and FC-77 (perfluoro-2-butyltetrahydrofuran, 24.3 g) were mixed. To the resulting clear liquid was added the drug, a homogenized dispersion of 4% egg yolk lecithin in water (0.60 g of the 4% dispersion, containing 0.024 g egg yolk lecithin). This material was administered via the technique outlined above to a rodent, who survived the procedure, and was returned to room air one day after completion of the liquid breathing. The rodent showed no ill effects, and was eating and grooming normally.

Example 8

Three rodents were subjected to liquid breathing of a perfluorodichlorooctane WIP emulsion having 4% by weight of an aqueous phase containing 2.0% egg yolk phospholipid surfactant. All survived the acute phase of the procedure. One died during the recovery phase, whereas the other two survived the entire protocol.

Example 9

Groups of five male Wistar rats (>250 gms) were inoculated with a Type III pneumococcal solution (0.4 ml, ≧3 MacFarland standard) by tracheal instillation. At t=4 hours the animals were anesthetized and mechanically ventilated. After 5 minutes, WIP formulations containing either 1 or 5 mg/ml of penicillin in the aqueous phase of the dispersion were instilled into the trachea and mechanical ventilation was continued for 15 minutes. Animals were assessed for mortality every 4–8 hours. Survival was analyzed by Cox's F-test (p≦0.05). The results are shown in the FIGURE. Animals treated with 5 ml (1 mg/ml) and 1.5 ml (5 mg/ml) WIP dispersions had significantly better survival rates than the animals receiving no treatment.

TABLE 1

| FORMULATION | | | | |
|---|---|---|---|---|
| WIP 1 | 0.08 w/v % Lecithin | 2 w/v % PF-octanol | 3.5 w/v % surfactant | 90.5 w/v % PFBTHF $H_2O$ q.s. |
| WIP 2 | 0.08 w/v % Lecithin | 2 w/v % PF-octanol | 3.5 w/v % surfactant | 90.5 w/v % PFBTHF $H_2O$ q.s. |
| WIP 3 | 0.08 w/v % Lecithin | 0.04 w/v % Doxorubicin | 3.5 w/v % surfactant | 92.5 w/v % PFBTHF |
| PIW 40 | 2 w/v % Lecithin | 2 w/v % Safflower Oil | 40 v/v % PFDCO | $H_2O$ q.s. |
| PIW 10 | 1.85 w/v % surfactant | 85.65 w % 0.9% saline | 10 v/v % PFMA | |
| PIW 50 | 10.0 w/v % surfactant | 50 w % 0.9% saline | 50 v/v % PFMA | |

TABLE 2

Arterial $pO_2$ Values (mm Hg)

| Formulation | Baseline @ 21% $O_2$ | Baseline @ 100% $O_2$ | 30 Minutes Post-PFC | Survival |
|---|---|---|---|---|
| WIP 1 | 117.2 | 645.9 | 468.6 | YES |
| WIP 2 | 69 | 498.5 | 583.6 | YES |
| WIP 3 | 137.7 | 647.1 | 544.4 | YES |
| PIW 40 | 113.2 | 617.6 | 76.6 | NO |
| PIW 10 | 128.8 | 569.5 | 59.4 | NO |
| PIW 50 | 95.1 | 481.8 | 71.8 | NO |

TABLE 3

| | pH Values | | | |
| Formulation | Baseline @ 21% O$_2$ | Baseline @ 100% O$_2$ | 30 Minutes Post-PFC | Survival |
| --- | --- | --- | --- | --- |
| WIP 1 | 7.426 | 7.448 | 7.374 | YES |
| WIP 2 | 7.506 | 7.519 | 7.456 | YES |
| WIP 3 | 7.414 | 7.437 | 7.371 | YES |
| PIW 40 | 7.394 | 7.342 | 7.24 | NO |
| PIW 10 | 7.448 | 7.417 | 7.295 | NO |
| PIW 50 | 7.452 | 7.463 | 7.295 | NO |

The preferred embodiments and examples discussed above are provided by way of illustration only and are not intended to limit the scope of the invention. For example, in many of the examples, the WIP dispersion has been discussed in conjunction with liquid breathing. However, the invention more generally encompasses simply delivering a drug to the lung of an animal by administering the inventive WIP dispersion to a portion of the lung, and the scope of the invention is to be determined by the following claims.

What is claimed is:

1. A homogenous water-in-perfluorochemical stable liquid dispersion, for acceptable therapeutic administration of a drug to the lung of an animal, comprising:
a perfluorochemical liquid, water, surfactant and drug, wherein said water is homogeneously dispersed in said perfluorochemical to form a stable water-in-perfluorochemical liquid dispersion, said perfluorochemical constituting greater than 50% by volume of said dispersion, said drug contained in said dispersion in an effective therapeutic amount.

2. The dispersion of claim 1 wherein said perfluorochemical is selected from the group consisting of perfluoro-n-butyltetrahydrofuran, perfluorodichlorooctane, perfluorobischlorobutylether, perfluorodecalin, perfluoromethyldecalin, perfluorodimethyldecalin, perfluorodimethyladamantane, perfluorooctylbromide, perfluoro-4-methyl-octahydroquinolidizine, perfluoro-N-methyl-decahydroquinoline, F-methyl-1-oxa-decalin, perfluoro-bicyclo(5.3.0)-decane, perfluorooctahydroquinolidizine, perfluoro-5,6-dihydro-5-decene, and perfluoro-4,5-dihydro-4-octene, chlorinated perfluorocarbons, and mixtures thereof.

3. The dispersion of claim 1 wherein said surfactant is selected from the group consisting of egg yolk phospholipid, a perfluorochemical alcohol, a polyalkyleneoxide, a 1,2-dialkylglycero-3-phosphoryl choline, a 1,3-dialkylglycero-2-phosphoryl choline, a fluorinated polyoxyethylene, and mixtures thereof.

4. The dispersion of claim 1 wherein said drug is selected from the group consisting of doxorubicin, deoxyribonuclease enzyme, a vector containing a normal cystic fibrosis transmembrane conductance regulator gene, pentamidine isethionate, amphotericin, a $\beta_2$ agonist, methotrexate, etoposide, a phospholipid surfactant, a penicillin, a cephalosporin, a sulphadrug, and a prodrug of any of the foregoing drugs, and mixtures thereof.

5. The dispersion of claim 1 wherein said perfluorochemical is present in an amount of from about 50% to about 99% by volume and said water is present in an amount of from about 50% to about 1% by volume.

6. The dispersion of claim 5 wherein said perfluorochemical is present in an amount of from about 85% to about 99% by volume and said water is present in an amount of from about 15% to about 1% by volume.

7. The dispersion of claim 1 wherein said surfactant is present in an amount of from about 0.5% to about 10% by weight.

8. The dispersion of claim 7 wherein said surfactant is present in an amount of from about 1% to about 4% by weight.

9. The dispersion of claim 1 wherein said drug is present in an amount of from about 0.001% to about 3% by weight.

10. The dispersion of claim 1 wherein said drug is present in an amount sufficient to treat a lung condition selected from the group consisting of cystic fibrosis, infant respiratory distress syndrome, a bacterial or fungal infection, asthma and lung cancer.

11. A method of delivering a drug to the lung of an animal comprising the step of:
administering a stable homogeneous, water-in-perfluorochemical liquid dispersion to the animal lung or a section thereof, said dispersion comprising a perfluorochemical liquid, water, surfactant and drug, said perfluorochemical constituting greater than 50% by volume of said dispersion, said drug contained in said dispersion in an effective therapeutic amount.

12. The method of claim 11 further comprising the step of delivering a breathable gas to the lung with a mechanical ventilator during said administration.

13. The method of claim 11 wherein said perfluorochemical is selected from the group consisting of perfluoro-n-butyltetrahydrofuran, perfluorodichlorooctane, perfluorobischlorobutylether, perfluorodecalin, perfluoromethyldecalin, perfluorodimethyldecalin, perfluorodimethyladamantane, perfluorooctylbromide, perfluoro-4-methyl-octahydroquinolidizineperfluoro-N-methyl-decahydroquinoline, F-methyl-1-oxa-decalin, perfluoro-bicyclo(5.3.0)-decane, perfluorooctahydroquinolidizine, perfluoro-5,6-dihydro-5-decene, and perfluoro-4,5-dihydro-4-octene, chlorinated perfluorocarbons, and mixtures thereof.

14. The method of claim 11 wherein said surfactant is selected from the group consisting of egg yolk phospholipid, a perfluorochemical alcohol, a polyalkyleneoxide, a 1,2-dialkylglycero-3-phosphoryl choline, a 1,3-dialkylglycero-2-phosphoryl choline, a fluorinated polyoxyethylene, and mixtures thereof.

15. The method of claim 11 wherein said drug is selected from the group consisting of doxorubicin, deoxyribonuclease enzyme, a vector containing a normal cystic fibrosis transmembrane conductance regulator gene, pentamidine isethionate, amphotericin, a $\beta_2$ agonist, methotrexate, etoposide, a phospholipid surfactant, a penicillin, a cephalosporin, a sulfadrug, and a prodrug of any of the foregoing drugs, and mixtures thereof.

16. The method of claim 11 wherein said perfluorochemical is present in an amount of from about 50% to about 99% by volume and said water is present in an amount of from about 50% to about 1% by volume.

17. The method of claim 16 wherein said perfluorochemical is present in an amount of from about 85% to about 99% by volume and said water is present in an amount of from about 15% to about 1% by volume.

18. The method of claim 11 wherein said surfactant is present in an amount of from about 0.5% to about 10% by weight.

19. The method of claim 18 wherein said surfactant is present in an amount of from about 1% to about 4% by weight.

20. The method of claim 11 wherein said drug is present in an amount of from about 0.001% to about 3% by weight.

21. The method of claim 11 conducted for treating a lung condition selected from the group consisting of cystic fibrosis, infant respiratory distress syndrome, a bacteria or fungal infection, asthma and lung cancer.

* * * * *